US00PP31054P2

(12) United States Plant Patent
Hanes

(10) Patent No.: US PP31,054 P2
(45) Date of Patent: Nov. 12, 2019

(54) ***PELARGONIUM* PLANT NAMED 'PEQZ0045'**

(50) Latin Name: *Pelargonium interspecific*
Varietal Denomination: PEQZ0045

(71) Applicant: SYNGENTA PARTICIPATIONS AG, Basel (CH)

(72) Inventor: Mitchell E. Hanes, Gilory, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/998,088

(22) Filed: Jun. 28, 2018

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./263.1, 324
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Pelargonium* plant named 'PEQZ0045' particularly distinguished by the bright pink inflorescences held above the medium-green foliage, very heat and drought tolerant with continuous color through the most extreme summer heat, and exceptional edema tolerance on a well-branched plant habit.

1 Drawing Sheet

Latin name of the genus and species of the plant claimed: *Pelargonium interspecific.*

Varietal denomination: 'PEQZ0045'.

BACKGROUND OF THE NEW PLANT

The present invention comprises a new *Pelargonium*, botanically known as *Pelargonium interspecific*, and hereinafter referred to by the variety name 'PEQZ0045'.

'PEQZ0045' is a product of a planned breeding program. The new cultivar 'PEQZ0045' has bright pink inflorescences held above the medium-green foliage, very heat and drought tolerant with continuous color through the most extreme summer heat, and exceptional edema tolerance on a well-branched plant habit.

'PEQZ0045' originates from a hybridization in a controlled breeding program made in September 2012, in a greenhouse in Guatemala. The female parent was an unpatented, proprietary plant of *P. interspecific* parentage, identified as '11100-7' with burgundy color florets.

The male parent of 'PEQZ0045' was an unpatented, proprietary plant of *P. interspecific* parentage, identified as '10301-1' with purple colored florets. The resultant seed was sown in November 2012 in a greenhouse in Gilroy, Calif.

The first act of asexual reproduction of 'PEQZ0045' was accomplished when vegetative stem tip cuttings were propagated from the initial selection in March 2013 in a greenhouse in Gilroy, Calif.

BRIEF SUMMARY OF INVENTION

Horticultural examination of plants grown from cuttings of the plant initiated in April 2013 in Gilroy, Calif., and continuing thereafter, has demonstrated that the combination of characteristics as herein disclosed for 'PEQZ0045' are firmly fixed and are retained through successive generations of asexual reproduction.

'PEQZ0045' has not been observed under all possible environmental conditions. The phenotype may vary significantly with variations in environment such as temperature, light intensity, and day length.

'PEQZ0045' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
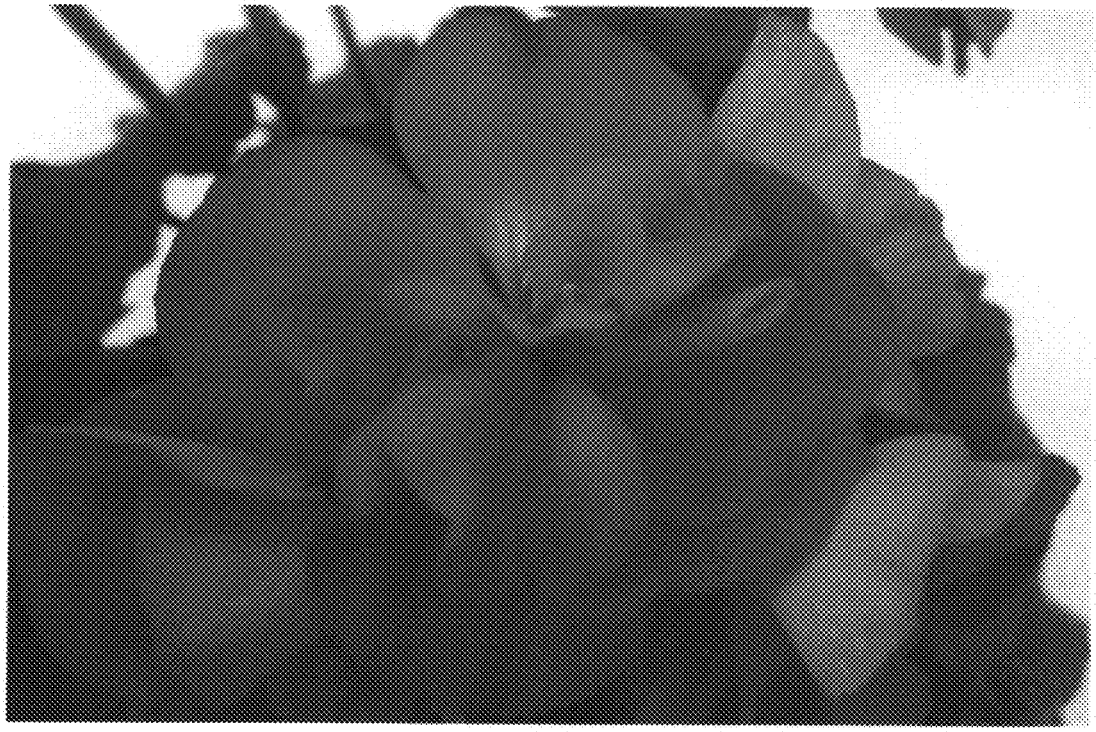
Figure 2:
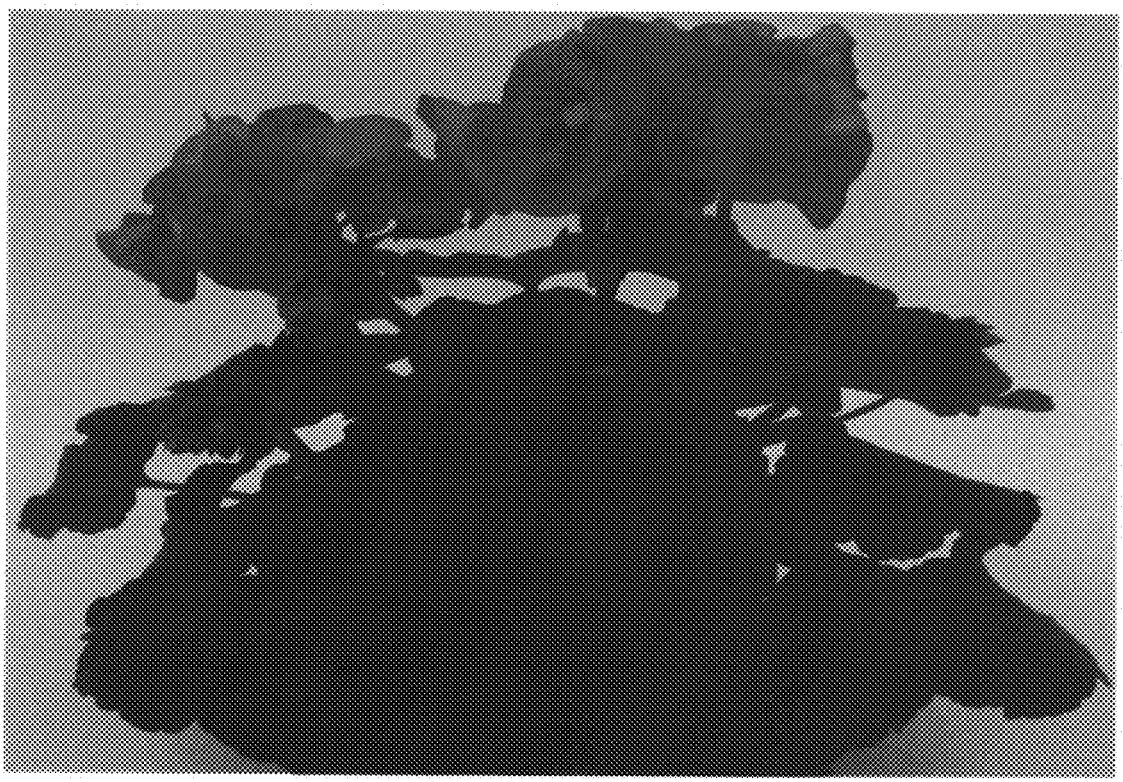

The accompanying photographic drawings show typical flower and foliage characteristics of 'PEQZ0045' with colors being as true as possible with an illustration of this type. The photographic drawings show in FIG. 1, a close-up of an inflorescence and in FIG. 2, 3 flowering plants of the new variety.

DETAILED BOTANICAL DESCRIPTION

The plant descriptions, measurements, and photo were taken in Gilroy, Calif. in December 2017 under natural light. These plants were approximately 10 weeks old and were grown in a 4.5 inch pots, in a greenhouse trial.

Color references are made to The Royal Horticultural Society Colour Chart (R.H.S.) 2015.

TABLE 1

DIFFERENCES BETWEEN THE NEW VARIETY 'PEQZ0045' AND A MOST SIMILAR VARIETY

| | 'PEQZ0045' | 'Calliope Large Pink' (U.S. Plant Pat. No. 28,288, 'PEQZ0009') |
|---|---|---|
| Leaf: | Darker green with light zone | Lighter shade of green |
| Floret petal: | Semi double | Semi double with more petals |
| Peduncle length: | Longer | Shorter |

Plant:

*Form, growth and habit.*—Upright, outwardly spreading and rounded growth habit, heat and drought tolerant with continuous color through the most extreme summer heat, edema tolerance, well-branched plant habit.

*Plant height.*—13-15.0 cm.

*Plant height (inflorescence included).*—22-24.0 cm.

*Plant width.*—28-31.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 137C deepening to RHS 174A.

*Immature leaf, lower surface.*—Closest to RHS 141C.

*Mature leaf, color upper surface.*—Closest to RHS N134A deepening to RHS 137A.

*Mature leaf, color lower surface.*—Closest to RHS 137D.

*Length.*—7-9.0 cm.

*Width.*—8-11.0 cm.

*Shape.*—Cordate.

*Base shape.*—Cordate.

*Apex shape.*—Acute to mucronate.

*Margin.*—Dentate to undulate.

*Texture upper side.*—Hirsute.

*Texture lower side.*—Hirsute.

*Leaf zonation.*—Faint.

*Color of veins, upper surface.*—RHS 137C.

*Color of veins, lower surface.*—RHS 137C.

*Pattern of veining.*—Palmate.

*Petiole color.*—RHS 137C.

*Petiole length.*—6-9.0 cm.

*Diameter of petiole.*—0.2 cm.

*Texture.*—Pilose, hirsute, glandular hairs.

Stem:

*Quantity of branches.*—4.

*Color of stem.*—Between RHS 144A to RHS 144B.

*Length of stem.*—3.7 cm.

*Diameter.*—0.5-0.7 cm.

*Length of internodes.*—2-2.5 cm.

*Texture.*—Sparsely hirsute, pilose, glandular hairs.

Peduncle:

*Color of peduncle.*—RHS 137C.

*Length of peduncle.*—14.5-16.0 cm.

*Peduncle diameter.*—0.3 cm.

*Texture.*—Hirsute, glandular hairs.

Pedicel:

*Color of pedicel.*—RHS 137B turning to RHS 187C.

*Length of pedicel.*—2.5-3.5 cm.

*Diameter of pedicel.*—0.15-0.2 cm.

*Texture.*—Sparsely pilose, glandular hairs.

Bud (just before opening):

*Color.*—RHS53C.

*Length.*—1.7-1.9 cm.

*Width.*—0.7-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—4, with 3 immature umbels and 2 mature.

*Fragrance.*—None.

*Umbel diameter.*—9-12.0 cm.

*Umbel depth.*—7-8.0 cm.

Corolla:

*Form.*—Semi-double.

*Number of petals.*—8.

*Diameter of flower.*—6-6.5 cm.

*Depth of flower.*—2-2.5 cm.

*Color upper petals, upper surface.*—Closest to RHS 67B with RHS NN155C and RHS 64A veining.

*Color upper petals, lower surface.*—Closest to RHS 62B with RHS 64B veining.

*Length of upper petals.*—3.0-3.5 cm.

*Width of upper petals.*—2.2-3.0 cm.

*Color lower petals, upper surface.*—Closest to RHS 67B.

*Color lower petals, lower surface.*—Closest to RHS 62B.

*Length of lower petals.*—3.0 cm.

*Width of lower petals.*—2.6-2.9 cm.

*Petal shape.*—Obovate to spathulate.

*Apex shape.*—Rounded to truncate.

*Margin.*—Entire.

*Base.*—Attenuate.

*Petal texture.*—Papillose on both surfaces.

Calyx:

*Number of sepals.*—5.

*Color of sepals.*—RHS 144B.

*Length of sepals.*—1.2-1.4 cm.

*Width of sepals.*—0.4-0.5 cm.

*Sepal shape.*—Lanceolate to linear.

*Apex shape.*—Acute to apiculate.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.0 cm.

*Style color.*—Closest to RHS 53B.

*Style length.*—0.3-0.4 cm.

*Stigma color.*—Closest to RHS 53B.

*Ovary color.*—RHS 144A.

*Ovary length.*—0.4-0.5 cm.

*Ovary diameter.*—0.2 cm.

Androecium:

*Number of stamens.*—5-7.

*Color of filaments.*—RHS NN155D.

*Length filaments.*—0.6-0.8 cm.

*Anther color.*—RHS 58A.

*Length of anthers.*—0.15-0.2 cm.

*Color of pollen.*—RHS N30A.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0045' substantially as illustrated and described herein.

* * * * *